United States Patent [19]

Budai et al.

[11] Patent Number: 5,234,934
[45] Date of Patent: Aug. 10, 1993

[54] AMINOPROPANOL DERIVATIVES, PROCESS FOR THEIR PREPARATION AND PHARMACEUTICAL COMPOSITIONS COMPRISING THE SAME

[75] Inventors: Zoltán Budai; Klára Reiter née Esses; Enikö Sziri née Kiszelly; Gizella Zsila; Gábor Gigler; Lujza Petöcz; Mária Szécsey née Hegedüs; Márton Fekete; Valéria Hoffmann; László Kápolnai, all of Budapest, Hungary

[73] Assignee: Egis Gyogyszergyar, Budapest, Hungary

[21] Appl. No.: 876,091

[22] Filed: Apr. 30, 1992

Related U.S. Application Data

[62] Division of Ser. No. 572,641, Aug. 27, 1990, Pat. No. 5,130,487.

[30] Foreign Application Priority Data

Aug. 25, 1989 [HU] Hungary .............................. 4401/89

[51] Int. Cl.$^5$ ........................................... A61K 31/445
[52] U.S. Cl. ..................... 514/331; 514/237.8; 514/255; 514/428; 544/165; 544/394; 544/401; 546/232; 548/569
[58] Field of Search ............... 546/235, 232; 564/256, 564/257; 514/640, 237.8, 428, 255; 544/165, 394, 401; 548/569

[56] References Cited

U.S. PATENT DOCUMENTS

| 4,766,151 | 8/1988 | Leclerc et al. | 514/640 |
| 4,803,286 | 2/1989 | Baldwin et al. | 514/431 |

FOREIGN PATENT DOCUMENTS 2135995 9/1984 United Kingdom .

*Primary Examiner*—Richard L. Raymond
*Assistant Examiner*—B. M. Burn
*Attorney, Agent, or Firm*—Beveridge, DeGrandi, Weilacher & Young

[57] ABSTRACT

The invention relates to novel racemic or optically active aminopropanol derivatives of formula I

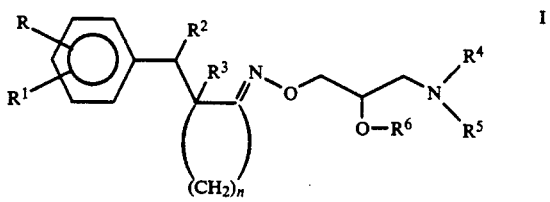

wherein
R and $R^1$ are independently hydrogen atom, halogen atom, lower alkoxy, or together represent a methylene dioxy group,
$R^2$ and $R^3$ together represent a chemical bond or independently stand for a hydrogen atom,
$R^4$ and $R^5$ are independently hydrogen atom, $C_{3-7}$ cycloalkyl group or straight or branched, saturated or unsaturated $C_{1-12}$ alkyl group optionally substituted by one or more dialkyl-aminoalkyl, dimethoxyphenyl or phenyl groups, or
$R^4$ and $R^5$ together with the adjacent nitrogen atom form a 4 to 7 membered ring optionally comprising an oxygen, sulfur or a further nitrogen atom, which ring is optionally substituted by a phenyl, benzyl or $C_{1-3}$ alkyl group and the said substituents may carry a hydroxyl group, one or two methoxy groups, halogen atoms or trifluoromethyl groups, or
$R^4$ and $R^5$ together with the adjacent nitrogen atom form a piperidine ring which is optionally substituted by a phenyl or benzyl group and, if desired, it comprises a double bond,
$R^6$ stands for hydrogen atom or benzoyl group, and
n represents an integer from 3 to 6,
acid-addition salts and quaternary ammonium derivatives thereof.

Further the invention relates to processes for preparing these compounds.

The compounds of the invention exert cardiac circulation controlling and/or improving, central nervous system tranquillizing and/or digestive system irregulations improving effects.

7 Claims, No Drawings

AMINOPROPANOL DERIVATIVES, PROCESS FOR THEIR PREPARATION AND PHARMACEUTICAL COMPOSITIONS COMPRISING THE SAME

This is a division of application Ser. No. 07/572,641 filed Aug. 27, 1990, now U.S. Pat. No. 5,130,487.

TECHNICAL FIELD

The present invention relates to novel, pharmaceutically active, racemic or optically active compounds of formula I

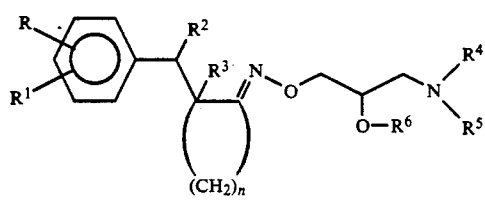

wherein
- R and $R^1$ are independently hydrogen atom, halogen atom, lower alkoxy, or together represent a methylene dioxy group,
- $R^2$ and $R^3$ together represent a chemical bond or independently stand for a hydrogen atom,
- $R^4$ and $R^5$ are independently hydrogen atom, $C_{3-7}$ cycloalkyl group or straight or branched, saturated or unsaturated $C_{1-12}$ alkyl group optionally substituted by one or more dialkyl-aminoalkyl, dimethoxyphenyl or phenyl groups, or
- $R^4$ and $R^5$ together with the adjacent nitrogen atom form a 4 to 7 membered ring optionally comprising an oxygen, sulfur or a further nitrogen atom, which ring is optionally substituted by a phenyl, benzyl or $C_{1-3}$ alkyl group and the said substituents may carry a hydroxy group, one or two methoxy groups, halogen atoms or trifluoromethyl groups, or
- $R^4$ and $R^5$ together with the adjacent nitrogen atom form a piperidine ring which is optionally substituted by a phenyl or benzyl group and, if desired, it comprises a double bond,
- $R^6$ stands for hydrogen atom or benzoyl group, and n represents an integer from 3 to 6, the acid-addition salts and quaternary ammonium derivatives thereof as well as cardiac circulation controlling and/or improving, central nervous system tranquilizing and/or digestive system irregulations improving pharmaceutical compositions containing these compounds.

The invention also relates to all of the possible stereoisomers of aminopropanol derivatives of formula I and to the mixture thereof.

The invention also covers the preparation of compounds of formula I.

BACKGROUND ART

Some aminohydroxy-propoxyimino derivatives are known in the art but their chemical structure and pharmaceutical activity are very different from those of the compounds of the present invention.

The fluorene derivative "IPS-339" of formula (a)

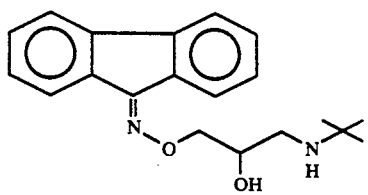

exhibits beta-adrenergic blocking effect.

The methyl cyclohexylketone derivative of formula (b)

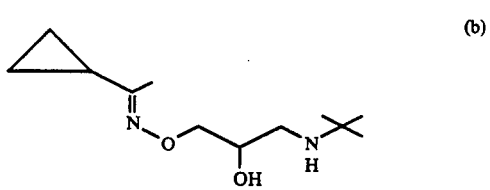

(known as Falintolol) also exhibits beta-adrenergic blocking activity.

Compound of formula (c) (known as Paradoxime)

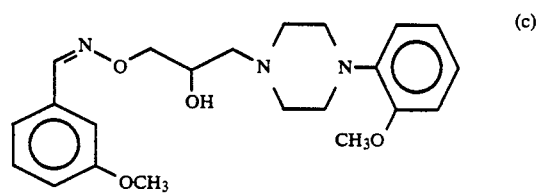

shows blood pressure reducing activity.

Peraclopone (compound of formula d)

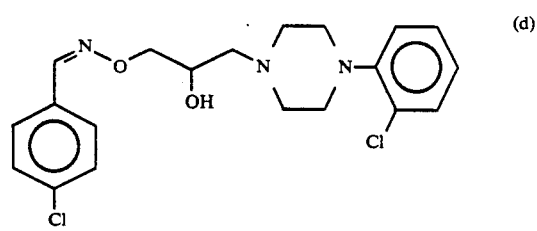

reduces the level of lipids.

Belgian patent specification No. 886,471 describes compounds of formula IX

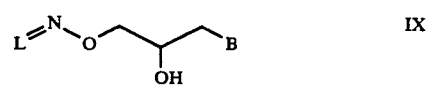

wherein L represents benzothiophene group, while B stands for a secondary amine group. The compounds exhibit beta-adrenergic blocking and antiarrhythmic activity.

Published PCT patent application No. 8402908 relates to carbostiryl ketoxime derivatives exhibiting not only beta-adrenergic blocking activity but antiglaucomic activity as well.

Belgian patent specification No. 838,440 describes beta-adrenergic blocking, blood pressure reducing and cardiovascular compounds of formula IX, wherein L represents a polycyclic ring (e.g. fluorene, indane, xanthane, tetrahydro naphthalene, etc.) or phenyl or naphthyl ketone and B always stands for a secondary amino group.

U.S. Pat. No. 4,652,586 relates to compounds of formula IX, wherein L is fluorene and B is a secondary amino group. The compounds reduce the inner pressure of eye and exhibit selective beta-two-adrenergic antagonist effect.

The chemical structure of the novel aminopropanol derivatives of formula I is basically different from that of the prior art compounds. The activity of the novel compounds of the invention is surprising and non-predictable as though few of the novel aminopropanol derivatives of formula I exhibit antiarrhythmic activity, this activity is not based on beta-adrenergic blocking effect.

The novel aminopropanol derivatives of formula I can be prepared in several manners.

They can be prepared e.g. by reacting a cycloalkane derivative of formula II

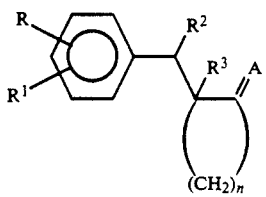

wherein R, $R^1$, $R^2$, $R^3$ and n are the same as defined hereinabove and A represents oxygen or sulfur atom, with a substituted alkane of formula III,

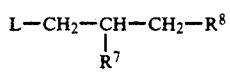

wherein L represents a group of formula $H_2N-O-$, or the acid-addition salt thereof, $R^7$ is hydroxyl and $R^8$ is a group of formula V,

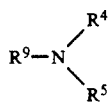

wherein $R^4$ and $R^5$ are the same as defined hereinabove and $R^9$ stands for a chemical bond.

According to an other embodiment of the process, the novel aminopropanol derivatives of formula I can be prepared by reacting a cycloalkane derivative of formula II, wherein R, $R^1$, $R^2$, $R^3$ and n are the same as defined hereinabove and A represents a group of formula $=N-OH$, with a halogen derivative of formula III, wherein L is halogen atom and $R^7$ and $R^8$ together represent an oxygen atom, and reacting a compound of formula VIII,

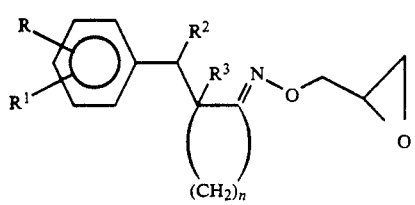

thus obtained, wherein R, $R^1$, $R^2$, $R^3$ and n are the same as defined hereinabove, with an amine of formula V, wherein $R^4$ and $R^5$ are the same as defined hereinabove and $R^9$ represents hydrogen atom.

According to an other preferred embodiment of the invention, the novel aminopropanol derivatives of formula I can be prepared by reacting a compound of formula II, wherein R, $R^1$, $R^2$, $R^3$ and n are the same as defined hereinabove and A represents oxygen or sulfur atom, with a glycol derivative of formula III, wherein L represents $H_2N-O-$ or the acid-addition salt thereof and $R^7$ and $R^8$ are independently hydroxyl groups, and reacting the glycol derivative of formula VI

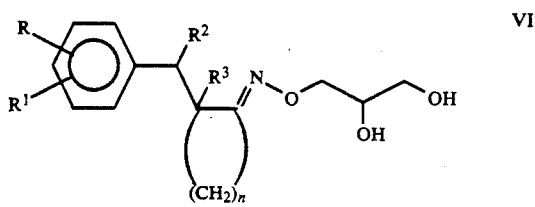

thus obtained, wherein R, $R^1$, $R^2$, $R^3$ and n are the same as defined hereinabove, first with thionyl chloride, then with an amine of formula V, wherein $R^4$ and $R^5$ are the same as defined hereinabove and $R^9$ represents hydrogen atom.

Those novel aminopropanol derivatives of formula I, wherein $R^6$ represents hydrogen atom, while R, $R^1$, $R^2$, $R^3$, $R^4$, $R^5$ and n are the same as defined hereinabove, can be reacted with a reactive benzoic acid derivative, preferably with benzoic acid anhydride, to obtain novel aminopropanol derivatives of formula I, wherein R, $R^1$, $R^2$, $R^3$, $R^4$, $R^5$ and n are the same as defined hereinabove and $R^6$ is benzoyl group.

Those compounds of formula II, wherein A stands for oxygen or sulfur atom, can be prepared according to J. Chem. Soc. 1955, 1126 or J. Am. Chem. Soc. 77, 624 (1955), while those, wherein A represents a group of formula $=N-OH$, can be produced e.g. according to Org. Synth. Coll. Vol. II. 70.

The compounds of formula III, wherein L is $H_2N-O-$, $R^7$ is hydroxyl and $R^8$ is a group of formula V, wherein $R^4$ and $R^5$ are the same as defined hereinabove and $R^9$ is a chemical bond, can be prepared according to J. Pharm. Sci. 58, 138 (1969).

The reaction of compounds of formula II with compounds of formula III—wherein R, $R^1$, $R^2$, $R^3$, A and n are the same as defined hereinabove, L is $H_2N-O-$ or the acid-addition salt thereof, $R^7$ is hydroxyl group and $R^8$ is a group of formula V, wherein $R^4$ and $R^5$ are the same as defined hereinabove and $R^9$ stands for a chemical bond—can preferably be carried out in an inert solvent or in a mixture of inert solvents. Such solvents may be e.g. alcohols, preferably ethanol or pyridine, triethyl amine, etc.

The temperature of the reaction can vary within wide ranges. The reaction can be completed even at room temperature, but according to our experiments the optimal reaction rate can be achieved at the boiling point of the reaction mixture.

If the novel aminopropanol derivatives of formula I are prepared by reacting a compound of formula II with a compound of formula III, wherein R, $R^1$, $R^2$, $R^3$ and n are the same as defined hereinabove, L is halogen atom, A is a group of formula $=N-OH$, while $R^7$ and $R^8$ together represent an oxygen atom, and the epoxy compound of formula VIII thus obtained is aminated with a compound of formula V, wherein $R^4$ and $R^5$ are the same as defined hereinabove and $R^9$ is hydrogen atom, then the reaction is carried out in an inert or relatively inert solvent in the presence of a basic condensing agent. As inert solvent preferably sodium amide or sodium hydride is used. Certainly the same result can be achieved when an other alkali metal amide or hydride is used as solvent. However, if an alkali metal is used as condensing agent, the alcohols, e.g. ethyl alcohol and propyl alcohols, are the most preferred solvents. If an alkali metal hydroxide is used as condensing agent, also water is a suitable solvent. (In this latter case water is a "relatively inert solvent" as it reacts with the epoxy ring after a longer reaction time and at higher temperatures.) The amination of the epoxy compound can be carried out in an inert medium, such as alcohols, e.g. ethanol, acetonitrile, dioxane, tetrahydrofurane, etc., but if the reaction is carried out by using amines of higher boiling point, it can be completed without solvent, too, as the amine serves also as a solvent.

If the novel aminopropanol derivatives of formula I are prepared by reacting a compound of formula II with a compound of formula III, wherein R, $R^1$, $R^2$, $R^3$ and n are the same as defined hereinabove, L is $H_2N-O-$ and $R^7$ and $R^8$ independently represent a hydroxyl group each, the reaction can be carried out in inert solvents, e.g. in alcohols, such as methyl or ethyl alcohol, benzene and the homologues thereof, ethers, etc. in the presence of an organic base, e.g. pyridine, lutidine, triethyl amine. The reaction can also be carried out by using the excess of the organic base as solvent. The glycol derivatives thus obtained can be reacted with thionyl chloride in an inert solvent, preferably in halogenated paraffins (such as dichloroethane, dichloromethane, chloroform, etc.), and the 1,2,3-dioxathiolane-2-oxide derivative thus obtained can be reacted with an amine of formula V, wherein $R^4$ and $R^5$ are the same as defined hereinabove and $R^9$ is hydrogen atom, in an inert solvent or without solvent.

Those novel aminopropanol derivatives of formula I, wherein $R^6$ represents hydrogen atom, while R, $R^1$, $R^2$, $R^3$, $R^4$, $R^5$ and n are the same as defined hereinabove, can be transformed into other compounds of formula I. They can be reacted with benzoic acid anhydride in an inert solvent to obtain derivatives of formula I, wherein R, $R^1$, $R^2$, $R^3$, $R^4$ and $R^5$ and n are the same as defined hereinabove and $R^6$ is a benzoyl group.

The novel aminopropanol derivatives of formula I can be transformed into pharmaceutically acceptable acid-addition salts or quaternary ammonium derivatives. For the preparation of the acid-addition salts hydrogen halides, sulfuric acid, phosphoric acid, tartaric acid, succinic acid, acetic acid, fumaric acid, maleic acid, methanesulfonic acid, propionic acid, etc. can be used. For the preparation of quaternary ammonium compounds the compounds of formula I are reacted with reactants suitable for quaternarization, e.g. with alkyl halides.

The novel aminopropanol derivatives of formula I may comprise one or two asymmetric carbon atoms depending on the character of the substitutents, thus one or more racemic or two or more optically active forms of compounds of formula I can be prepared. The invention covers all of the racemic and optically active forms of compounds of formula I. If the former compounds or intermediates are prepared in the form of a diastereomeric mixture, then they can be separated into the racemic or optically active isomers in a manner known per se, by e.g. fractionated distillation, crystallization, chromatography or by forming diasteromeric salts with the aid of optically active acids, such as tartaric acid, dibenzoyl tartaric acid or camphorsulfonic acid.

According to our experiments the novel aminopropanol derivatives of formula I proved to be biologically active upon testing for pharmaceutical activity. Among the observed biological activities the most significant ones are the antianginal and/or antiarrhythmic activity, inhibition of stomach secretion (gastric acid secretion), local anaesthetic, tranquillo-sedative, antiinflammatory, analgesic and in some cases calcium antagonistic activity.

The test for acute toxicity was carried out by using 10 white mice (CFLP strain) (both male and female), weighing 18 to 22 g in each dose group. The compounds of the invention were administered orally in a dose of 20 ml/kg.

After the administration of the compounds the animals were observed for 14 days. The animals were kept in a plastic box on wood chips in a room of room temperature. They could consume tap water and standard mouse feed ad libitum. The toxicity data were determined by the method of Litchfield and Wilcoxon (Litchfield, J. T., Wilcoxon, F. W.: J. Pharmacol. Exp. Ther. 96, 99/1949/).

| Compound according to working example No. | $LD_{50}$ mg/kg po. |
|---|---|
| 4 | 1800 |
| 1 | 400 |
| 28 | 1500 |
| 14 | 900 |
| 27 | about 1000 |
| 29 | 1300 |
| 32 | more than 2000 |
| 31 | about 1000 |
| 30 | 1100 |
| 22 | 900 |
| 23 | 130 |
| 18 | more than 1000 |
| 26 | more than 1000 |
| 35 | 600 |
| 25 | 900 |
| 20 | more than 1000 |
| 36 | 700 |
| 42 | more than 1000 |
| 37 | more than 1000 |
| 33 | more than 1000 |
| 43 | 800 |
| 19 | 800 |
| 34 | more than 1000 |
| 21 | 700 |
| 2 | 600 |
| 10 | 900 |
| 8 | 800 |
| 9 | 700 |
| 15 | more than 1000 |
| 7 | more than 1000 |
| 38 | more than 1000 |
| 16 | more than 1000 |
| 17 | more than 1000 |
| 6 | more than 1000 |
| 11 | more than 1000 |
| 3 | more than 1000 |
| 5 | more than 1000 |
| 39 | more than 1000 |
| 24 | more than 1000 |
| 44 | 600 |
| 46 | more than 1000 |
| 13 | more than 1000 |
| 12 | 1000 |
| 47 | 700 |
| 45 | more than 1000 |

| Compound according to working example No. | LD$_{50}$ mg/kg po. |
| --- | --- |
| 41 | more than 1000 |
| 40 | 800 |
| 69 | more than 1000 |
| 49 | more than 1000 |
| 48 | more than 1000 |
| 50 | 1000 |
| 52 | more than 1000 |
| 51 | 100 to 500 |
| 53 | more than 1000 |
| 54 | 600 |
| 55 | more than 1000 |

The narcosis potentiating effect of the compounds of the invention were examined on white mice, with 6 animals in each group. The mice were administered orally with the compounds of the invention, then both the control and the test groups were intravenously added 40 mg/kg of hexobarbital in order to make the mice sleep (Kaergard et al.).

Those animals were considered as showing positive reaction whose sleeping time was 2.5 times higher than the average sleeping time of the control group (Kaergard Nielsen, G., Magnussen, M. P., Kampmann, E., Frey, H. H.: Archt. Int. Pharmacodyn. 2, 170 (1967), and the ED$_{50}$ data were calculated by using the transformed data thus obtained.

| Compound of working example No. | ED$_{50}$ mg/kg po. | TI |
| --- | --- | --- |
| 28 | 75 | 20 |
| 14 | 80 | 11 |
| 27 | 35 | 29 |
| 29 | 30 | 43 |
| 32 | 50 | >40 |
| 23 | 16 | 8 |
| 18 | 25 | >40 |
| 26 | 140 | >7 |
| 35 | 11.5 | 52 |
| 20 | 21.5 | >46.5 |
| 36 | 14 | 50 |
| 42 | 14.5 | >69 |
| 37 | 50 | >20 |
| 43 | 50 | 16 |
| 19 | 26 | 31 |
| 34 | 145 | >7 |
| 9 | 30 | 23 |
| 7 | 70 | 14 |
| 38 | 61 | 16 |
| Chlordiazepoxide | 10 | 62 |
| Meprobamate | 260 | 4.2 |

TESTING OF ANTIARRYTHMIC EFFECT ON RATS

Method

The test was carried out by using the modified method of Marmo et al. on rats weighing 160 to 200 g. The animals were narcotised by ethyl uretane (1.2 g/kg ip.). Aconitin was administered intravenously in a dose of 75 /ug/kg in the form of a bolus injection. The ECG alterations were monitored in standard II lead by 5 minutes after the administration of aconitine. The observed alterations were classified into classes 0 to 5. The compounds of the invention were administered 2 minutes or 60 minutes before the parenteral or oral administration of aconitine, respectively.

Evaluation class 1: sometimes an extrasystole occurs
class 2: each second one is an extrasystole
class 3: extrasystoles in groups
class 4: each one is an extrasystole
class 5: fibrillation, death
(Marmo, E., DiGiacomo, S., Imperatore, A.: Arzeimittel-Forschung 20, 12/1970/)

Intravenous Administration

| Compound according to working example No. | Effect % 4 mg/kg iv. dose | ED$_{50}$ mg/kg iv. |
| --- | --- | --- |
| 23 | −83 | 0.36 |
| 1 | −89.5 | 1.21 |
| 14 | −83 | 1.64 |
| 35 | −100 | 1.84 |
| 19 | −76 | 3.29 |
| 18 | −50 | — |
| 10 | −47 | — |
| 21 | −46 | — |
| 2 | −43 | — |
| 48 | −43.5 | — |
| 54 | −56.0 | 3.47 |
| Mexiletine | −21 | — |
| Dilthiazem | −27 | — |
| Quinidine | −29 | 9.85 |
| Propranolol | −7 | 5.81 |

Per Os Administration

| Compound according to working example No. | Effect % 100 mg/kg dose | ED$_{50}$ mg/kg | LD$_{50}$ mg/kg po. on rat. | TI |
| --- | --- | --- | --- | --- |
| 1 | −100% | 27.3 | 1763.5 | 64.6 |
| Quinidine | −52% | about 100 | 1132 | about 11.3 |
| Propanolol | −50% | | | |
| Pindolol | −52% | | | |

The compound according to Example 1 administered orally has a multiplied effect compared to the control compounds regarding the absolute dose, its therapeutical activity range is 5.8 times higher than that of Quinidine.

Antianginal Effect on Rats

The test was carried out by using rats weighing 180 to 220 g. The animals were narcotised by chloralose urethane (70 to 700 mg/kg ip.). The ECG alterations were registered in standard II lead with the aid of needle electrodes. The antianginal effect was measured with Nieschultz's method. The coronary insufficiency was caused by vasopressine (1 NE/kg, iv.). The size of the T-wave was measured before and after administration of vasopressine in both the control and test groups. The compounds of the invention were administered 2 minutes before the administration of vasopressine. (Nieschulz, O., Popendiker, K., Hoffmann, I.: Arzneimittel-Forschung 5, 680/1955/)

| Compound according to working example No. | ED$_{50}$ mg/kg iv. |
| --- | --- |
| 26 | about 2.0 |
| 36 | 1.28 |
| 43 | about 2.0 |
| 10 | 1.62 |
| 11 | 0.93 |

-continued

| Compound according to working example No. | $ED_{50}$ mg/kg iv. |
|---|---|
| 44 | 1.93 |
| 47 | 1.29 |
| 51 | 0.43 |
| 55 | 1.77 |
| Prenilamine | 6.5 |

Local Analgesic Effect

The tests were carried out according to Truant d'Amato's method. 0.2 ml of test material was injected around the nervus ischiadicus in the middle of femur with a needle of 1 cm length. The criterion of analgesic effect was the lack of the motoric control of foot muscles.

The duration of effect was registered and the 50 percentile effective concentration ($EC_{50}$) was calculated on the basis of the dose-effect curve. Lidocain was used as comparative material. (Truant, A. P., D'Amato, D.: Acta Chir Scand. 116, 351/1958/)

| Compound according to working example No. | $EC_{50}\%$ | Duration of effect in a conc. of 0.5% |
|---|---|---|
| 1 | 0.04 | within 2.5 to 17 hours |
| 26 | 0.22 | 49 minutes |
| 21 | 0.24 | 89 minutes |
| 46 | 0.19 | 81 minutes |
| 47 | 0.18 | 93 minutes |
| 40 | 0.19 | 68 minutes |
| 48 | 0.31 | 122 minutes |
| 51 | 0.28 | 103 minutes |
| Lidocain | 0.19 | 34 minutes |

Gastric Acid Secretion Test

The test was carried out according to Shay's operational method. Rats weighing 200 to 250 g were fastened for 48 hours. On the day of the test the pylorus of the animals was bound under ether narcosis. The test compounds were administered orally 3 hours before the operation. The animals of the control group were administered with the carrier only. 4 hours after the operation the stomach was removed, the content thereof was centrifuged and the amount of free acid was determined by titration with 0.1N sodium hydroxide.

The activity of the compounds of the present invention reach or exceed the activity of Cimetidine and highly exceed the secretion inhibiting effect of Trithiozine. (Shay, H., Komarov, S. A., Fels, S. S., Meranze, D., Gruenstein, M., Siplet, H.: Gastroenterology 5, 45/1945/)

| Compound according to working example No. | Dose po. mg/kg | Inhibition of free acid, % |
|---|---|---|
| 4 | 200 | 77 |
| 1 | 200 | 70 |
| 29 | 260 | 87 |
| 32 | 400 | 62 |
| 18 | 200 | 68 |
| 26 | 200 | 92 |
|  | 100 | 66 |
| 33 | 200 | 100 |
| 43 | 160 | 32 |
| 11 | 200 | 62 |
| 13 | 200 | 74 |
| 45 | 200 | 100 |
| 41 | 200 | 67 |
| 40 | 160 | 57 |

-continued

| Compound according to working example No. | Dose po. mg/kg | Inhibition of free acid, % |
|---|---|---|
| 48 | 100 | 75 |
| Cimetidine | 100 | 66 |
|  | 200 | 91 |
| Trithiozine | 100 | 30 |
|  | 400 | 63 |

Effect Exerted on the Peristalty of Stomach and Intestines

The antiperistaltic effect of the compounds was examined by the method of Stickney et al. on white mice of both sexes, weighing 20 to 25 g. The compounds to be tested were administered per os 60 minutes before the addition of carbon suspension to groups containing 10 mice each. The animals of the control groups were treated at the same time and in the same manner with the carrier only. The mice were killed 10 minutes after the addition of the carbon suspension, and the whole length of the intestines as well as the length of the intestines filled with carbon suspension were measured.

| Compound according to working example No. | $ED_{50}$ mg/kg po. | TI |
|---|---|---|
| 1 | about 80 | about 5 |
| 20 | about 100 | about 10 |
| 36 | about 100 | about 7 |
| 15 | 140 | 7 |
| 38 | 23 | 44 |
| 6 | 140 | 7 |
| 11 | 100 | 10 |
| 5 | 70 | 14 |
| 30 | 130 | 8 |
| 24 | about 150 | about 7 |
| 12 | about 200 | about 5 |
| Papaverine | above 280 mg/kg (36% inhibition) $ED_{50}$ cannot be determined | |

The therapeutic index (TI) indicated in the above Tables was calculated as follows:

$$\text{Therapeutic index } TI = \frac{LD_{50}}{ED_{50}}$$

The compounds of formula I according to the invention can well be absorbed if administered either orally or parenterally. The compound of formula (e) described in U.S. Pat. No. 4,621,101 is known as an excellent antiarrhythmic agent. This compound has an $ED_{50}$ per os/$ED_{50}$ iv=32.77/0.54=60.5 value. The compound according to Example 1 of the present specification has an $ED_{50}$ per os/$ED_{50}$ iv=24.36/1.21=20.6 value, and this means that the absorption values of this compound are much better than that of the cited compound of formula (e) used as standard for comparison.

The compounds of formula I, the acid-addition salts or quaternary ammonium derivatives thereof can be transformed into especially cardiac circulation regulating and/or improving, central nervous system tranquillizing and digestive system irregulations improving pharmaceutical formulations in a manner known per se by using pharmaceutically acceptable carriers and/or diluents and/or excipients. One dose of the pharmaceutical composition may comprise 0.5 to 500 mg of compounds of formula I, the acid-addition salts or the quaternary ammonium derivatives thereof.

The invention is further illustrated by the following, non-limiting examples. (The melting points and boiling points appearing in the examples are not corrected.)

EXAMPLE 1

R,S-2-(E)-Phenylmethylene-1-(E)-{3-[bis-(1-methylethyl)-amino]-2-hydroxy-propoxyimino}-cyclohexane a) 2-(E)-Phenylmethylene-cyclohexan-1-one-(E)-oxime (20.13 g; 0.1 mole) is transformed into a salt with the aid of sodium hydride (4.8 g; 0.1 mole, 50% oily dispersion) in the mixture of dimethyl formamide and benzene, and this salt is condensed with 1-chloro-2,3-epoxypropane (10.18 g; 0.11 mole) at a temperature of 40° to 50° C. The stirring is continued until the oxime cannot be detected in the reaction mixture by thin-layer chromatography (Kieselgel 60 $F_{254}$; eluent: 4:1 mixture of n-hexane and dioxane). The reaction mixture is washed with water, the solvent is distilled off and the product recovered is used without further purification.

Yield: 26.2 g (96.3%) yellowish oil b) The product obtained according to point a) (26.2 g; 0.96 mole) is reacted with diisopropyl amine (11.13 g; 0.11 mole) at the boiling temperature of the reaction mixture. The boiling is continued until the starting material cannot be detected by thin-layer chromatography (Kieselgel 60 $F_{254}$; eluent: a 4:1 mixture of benzene:methanol).

The solvent is distilled off and the product is purified by precipitation from acidic to alkaline medium.

Yield: 32.0 g (89%) Melting point: 47°–49° C. (n-hexane)

Analysis for formula $C_{22}H_{34}N_2O_2$: Calculated: C=75.70%; H=9.56%; N=7.81%; Found: C=75.63%; H=9.42%; N=7.93%.

UV: $\lambda_{max}=276$ nm ($\epsilon=14\ 802$)

(E)-2-Butenedioate (1/1) Melting point: 173°–6° C.

Analysis for formula $C_{26}H_{38}N_2O_6$ (474.58): Calculated: C=65.79%; H=8.07%; N=5.90%; Found: C=66.35%; H=8.16%; N=5.94%.

UV: $_{max}=273$ nm (=14 377)

Hydrochloride (1/1) Melting point: 189°–92° C.

Analysis for formula $C_{22}H_{35}ClN_2O_2$ (394.977): Calc.: C=66.90%; H=8.93%; N=6.39%; Cl=8.98%; Found: C=65.60%; H=8.86%; N=7.13%; Cl=8.99%.

Hydrobromide (1/1) Melting point: 180°–83° C.

Analysis for formula $C_{22}H_{35}BrN_2O_2$ (439.436): Calc.: C=60.13%; H=8.03%; N=6.38%; Br=18.29%; Found: C=59.86%; H=7.99%; N=6.33%; Br=18.17%.

Butanedioate (1/1) Melting point 129°–31° C.

Analysis for formula $C_{26}H_{40}N_2O_6$ (476.6): Calculated: C=65.52%; H=8.46%; N=5.88%; Found: C=65.33%; H=8.44%; N=5.91%.

Ethanedioate (1/1)

Analysis for formula $C_{24}H_{36}N_2O_6$ (448.55): Calculated: C=59.98%; H=7.55%; N=5.83%; Found: C=59.77%; H=7.53%; N=5.85%.

(Z)-2-Butenedioate (1/1)

Analysis for formula $C_{26}H_{38}N_2O_6$ (474.58): Calculated: C=65.79%; H=8.07%; N=5.90%; Found: C=66.11%; H=8.00%; N=5.88%.

EXAMPLE 2

R,S-2-(E)-Phenylmethylene-1-(E)-[3-(1,1-dimethylethyl-amino)-2-hydroxy-propoxyimino]-cyclohexane a) The process of Example 1/a is followed.

b) The process of Example 1/b is followed except that 2-amino-2-methyl propane (8.05 g; 0.11 mole) is used instead of diisopropyl amine.

Yield: 27.4 g (83%).

(E)-2-Butenedioate (2/1) Melting point: 182°–5° C.

Analysis for formula $C_{22}H_{32}N_2O_4$ (388.50): Calculated: C=68.01%; H=8.38%; N=7.21%; Found: C=65.57%; H=8.36%; N=7.08%.

UV: $\lambda_{max}=274$ nm ($\epsilon=15\ 120$)

EXAMPLE 3

R,S-2-(E)-Phenylmethylene-1-(E)-(3-hexylamino-2-hydroxy-propoxyimino)-cyclohexane The process of Example 1 is followed except that instead of 1-chloro-2,3-epoxypropane 1-bromo-2,3-epoxypropane (15.07 g; 0.11 mole) and instead of diisopropyl amine n-hexylamine (11.13 g; 0.11 mole) are used.

Yield: 28.3 g (79%)

(E)-2-Butenedioate (2/1) Melting point: 155°–8° C.

Analysis for formula $C_{24}H_{36}N_2O_4$ (416.55): Calculated: C=69.20%; H=8.71%; N=6.73%; Found: C=68.85%; H=8.68%; N=6.75%.

UV: $\lambda_{max}=276$ nm ($\epsilon=15\ 700$)

EXAMPLE 4

R,S-2-(E)-Phenylmethylene-1-(E)-[3-(4-methyl-1-piperazinyl)-2'-hydroxy-propoxyimino]-cyclohexane The process of Example 1 is followed except that instead of ethanol methanol, and instead of diisopropyl amine 1-methylpiperazine (11.0 g; 0.11 mole) are used.

Yield: 32.9 g (92%)

(E)-2-Butenedioate (1/2) Melting point: 179°–181° C.

Analysis for formula $C_{29}H_{39}N_3O_{10}$ (589.68): Calculated: C=59.07%; H=6.67%; N=7.13%; Found: C=58.91%; H=6.68%; N=7.20%.

UV: $\lambda_{max}=275$ nm ($\epsilon=12\ 995$)

EXAMPLE 5

R,S-2-(E)-Phenylmethylene-1-(E)-[3-(4-phenyl-1-piperazinyl)-2-hydroxy-propoxyimino]-cyclohexane a) The process of Example 1/a is followed.

b) The process of Example 1/b is followed except that 1-phenyl-piperazine (17.85 g; 0.11 mole) is used instead of diisopropyl amine.

Yield: 38.2 g (91%).

(E)-2-Butenedioate (2/1) Melting point: 164°–7° C.

Analysis for formula $C_{28}H_{35}N_3O_4$ (477.58): Calculated: C=70.41%; H=7.39%; N=8.80%; Found: C=70.05%; H=7.41%; N=8.68%.

UV: $\lambda_{max1}=251$ nm ($\epsilon=20\ 501$), $\lambda_{max2}=274$ nm ($\epsilon=17\ 436$)

EXAMPLE 6

R,S-2-(E)-Phenylmethylene-1-(E)-[3-(4-phenylmethyl-1-piperazinyl)-2-hydroxy-propoxyimino]-cyclohexane a) The process of Example 1/a is followed.

b) The process of Example 1/b is followed except that 1-phenylmethyl-piperazine (19.39 g; 0.11 mole) is used instead of diisopropyl amine.

Yield: 39.0 g (90%).

(E)-2-Butenedioate (1/2) Melting point: 179°–83° C.

Analysis for formula $C_{35}H_{43}N_3O_{10}$ (665.71): Calculated: C=63.14%; H=6.51%; N=6.31%; Found: C=63.23%; H=6.44%; N=6.19%.

UV: $\lambda_{max}=270$ nm ($\epsilon=16\ 304$)

EXAMPLE 7

R,S-2-(E)-Phenylmethylene-1-(E-[3-(3,4-dimethoxyphenyl-ethylamino)-2-hydroxy-propoxyimino]-cyclohexane The process of Example 1 is followed except that 3,4-dimethoxyphenyl-ethylamine (19.94 g; 0.11 mole) is used instead of diisopropyl amine.

Yield: 34.2 g (78%).

(E)-2-Butenedioate (2/1) Melting point: 94°–98° C.

Analysis for formula $C_{28}H_{36}N_2O_6$ (378.23): Calculated: C=67.72%; H=7.31%; N=5.64%; Found: C=66.87%; H=7.22%; N=5.76%.

UV: $\lambda_{max}$=270 nm ($\epsilon$=17 822)

EXAMPLE 8

R,S-2-(E)-Phenylmethylene-1-(E)-(3-pyrrolidinyl-2-hydroxy-propoxyimino)-cyclohexane The process of Example 1 is followed except that pyrrolidine (7.82 g; 0.11 mole) is used instead of diisopropyl amine.

Yield: 27.3 g (83%).

(E)-2-Butenedioate (2/1) Melting point: 168°–174° C.

Analysis for formula $C_{22}H_{30}N_2O_4$ (386.48): Calculated: C=68.36%; H=7.92%; N=7.25%; Found: C=68.86%; H=8.08%; N=7.28%.

UV: $\lambda_{max}$=284 nm ($\epsilon$=14 556)

EXAMPLE 9

R,S-2-(E)-Phenylmethylene-1-(E)-(3-piperidinyl-2-hydroxypropoxyimino)-cyclohexane The process of Example 1 is followed except that piperidine (9.37 g; 0.11 mole) is used instead of diisopropyl amine.

Yield: 29.7 g (87%).

(E)-2-Butenedioate (2/1) Melting point: 167°–9° C.

Analysis for formula $C_{23}H_{32}N_2O_4$ (400.51): Calculated: C=68.97%; H=8.05%; N=7.00%; Found: C=68.57%; H=8.01%; N=7.12%.

UV: $\lambda_{max}$=276 nm ($\epsilon$=13 852)

EXAMPLE 10

R,S-2-(E)-Phenylmethylene-1-(E)-(3-hexamethyleneimino-2-hydroxypropoxyimino)-cyclohexane The process of Example 1 is followed except that hexahydro-1H-azepine (10.91 g; 0.11 mole) is used instead of diisopropyl amine.

Yield: 28.9 g (81%).

(E)-2-Butenedioate (2/1) Melting point: 163°–6° C.

Analysis for formula $C_{24}H_{34}N_2O_4$ (414.53): Calculated: C=69.53%; H=8.27%; N=6.76%; Found: C=69.55%; H=8.33%; N=6.84%.

UV: $\lambda_{max}$=286 nm ($\epsilon$=14 044)

EXAMPLE 11

R,S-2-(E)-Phenylmethylene-1-(E)-[3-(3-dimethylamino-1-propylamino)-2-hydroxy-propoxyimino]-cyclohexane The process of Example 1 is followed except that 3-dimethylamino-1-propylamine (11.24 g; 0.11 mole) is used instead of diisopropyl amine.

Yield: 27.0 g (75%).

(E)-2-Butenedioate (1/2) Melting point: 176°–9° C.

Analysis for formula $C_{29}H_{41}N_3O_{10}$ (591.64): Calculated: C=58.87%; H=6.99%; N=7.10%; Found: C=59.20%; H=7.11%; N=7.20%.

UV: $\lambda_{max}$=270 nm ($\epsilon$=16 606)

EXAMPLE 12

R,S-2-(E)-Phenylmethylene-1-(E)-{[4-(4-chlorophenyl)-1-piperazinyl]-2-hydroxy-propoxyimino}-cyclohexane The process of Example 1 is followed except that 1-(4-chlorophenyl)-piperazine (21.63 g; 0.11 mole) is used instead of diisopropyl amine.

Yield: 40.9 g (90%).

(E)-2-Butenedioate (1/2) Melting point: 184°–7° C.

Analysis for formula $C_{34}H_{40}ClN_3O_{10}$ (686.14): Calculated: C=$^{59.51}$%; H=5.88%; N=6.12%; Cl=5.17%; Found: C=59.80%; H=5.92%; N=6.23%; Cl=5.05%.

UV: $\lambda_{max}$=272 nm ($\epsilon$=15 531)

EXAMPLE 13

R,S-2-(E)-Phenylmethylene-1-(E)-}[4-(2-hydroxyethyl)-1-piperazinyl]-2-hydroxy-propoxyimino}-cyclohexane The process of Example 1 is followed except that 2-(2-hydroxyethyl)-piperazine (14.32 g 0.11 mole) is used instead of diisopropyl amine.

Yield: 32.1 g (83%).

(E)-2-Butenedioate (1/2) Melting point: 164°–7° C.

Analysis for formula $C_{30}H_{41}N_3O_{11}$ (619.65): Calculated: C=58.15%; H=6.67%; N=6.78%; Found: C=57.83%; H=6.63%; N=6.88%.

UV: $\lambda_{max}$=274 nm ($\epsilon$=15 908)

EXAMPLE 14

R,S-2-(E)-Phenylmethylene-1-(E)-{3-[bis-(1-methylethyl)-amino]-2-hydroxy-propoxyimino}-cycloheptane a) 2-(E)-Phenylmethylene-cycloheptan-1-one-(E)-oxime (21.53 g; 0.1 mole) is transformed into a salt with the aid of freshly prepared sodium methylate (5.4 g; 0.1 mole) and the salt is condensed with 1-chloro-2,3-epoxypropane (10.18 g; 0.11 mole) in dimethyl formamide at a temperature of 40° to 50° C. Further on the process of Example 1/a is followed.

b) The process of Example 1/b is followed.

Yield: 317 g (85%).

(E)-2-Butenedioate (1/1) Melting point: 148°–52° C.

Analysis formula $C_{27}H_{40}N_2O_6$ (488.61): Calculated: C=66.36%; H=8.25%; N=5.73%; Found: C=66.36%; H=8.18%; N=5.79%.

UV: $\lambda_{max1}$=261 nm ($\epsilon$=16 627), $\lambda_{max2}$=261 nm ($\epsilon$=16 675)

EXAMPLE 15

R,S-2-(E)-Phenylmethylene-1-(E)-(3-morpholino-2-hydroxypropoxyimino)-cycloheptane a) The process of Example 14/a is followed.

b) The process of Example 1/b is followed except that morpholine (9.58 g; 0.11 mole) is used instead of diisopropyl amine.

Yield: 33.0 g (92%).

(E)-2-Butenedioate (1/1) Melting point: 133°–4° C.

Analysis for formula $C_{25}H_{34}N_2O_7$ (474.54): Calculated: C=63.27%; H=7.22%; N=5.90%; Found: C=63.17%; H=7.25%; N=5.81%.

UV: $\lambda_{max}$=257 nm ($\epsilon$=16 706)

EXAMPLE 16

R,S-2-(E)-Phenylmethylene-1-(E)-[3-(1,1-dimethylpropin-2-yl)amino-2-hydroxy-propoxyimino]-cycloheptane The process of Example 14 is followed except that 1,1-dimethylpropin-2-yl-amine (9.14 g; 0.11 mole) is used instead of diisopropyl amine.

Yield: 29.0 g (82%).

(E)-2-Butenedioate (1/1) Melting point: 162°–5° C.

Analysis for formula $C_{26}H_{34}N_2O_6$ (470.55): Calculated: C=66.36%; H=7.28%; N=5.95%; Found: C=66.96%; H=7.31%; N=5.93%.

UV: $\lambda_{max}=261$ nm ($\epsilon=16\ 612$)

EXAMPLE 17

R,S-2-(E)-Phenylmethylene-1-(E)-[3-(4-methyl-1-piperazinyl)-2-hydroxy-propoxyimino]-cycloheptane The process of Example 14 is followed except that 1-methyl piperazine (11.0 g; 0.11 mole) is used instead of diisopropyl amine.

Yield: 33.4 g (90%).

(E)-2-Butenedioate (1/2) Melting point: 200°–4° C.

Analysis for formula $C_{30}H_{41}N_3O_{10}$ (603.65): Calculated: C=59.69%; H=6.85%; N=6.96%; Found: C=59.47%; H=6.77%; N=6.84%.

UV: $\lambda_{max}=258$ nm ($\epsilon=17\ 661$)

EXAMPLE 18

R,S-2-(E)-Phenylmethylene-1-(E)-(3-morpholino-2-hydroxy-propoxyimino)-cyclooctane a) The process of Example 1/a is followed except that toluene is used instead of benzene and 2-(E)-phenylmethylene-cyclooctane-1-one-(E)-oxime (22.93 g; 0.1 mole) is used as oxime.

Yield: 29.5 g (98.4%) oil b) The process of Example 15/b is followed.

Yield: 30.2 g (80%).

(E)-2-Butenedioate (1/1) Melting point: 150°–3° C.

Analysis for formula $C_{26}H_{36}N_2O_7$ (488.6): Calculated: C=63.91%; H=7.42%; N=5.73%; Found: C=64.13%; H=7.45%; N=5.70%.

UV: $\lambda_{max}=265$ nm ($\epsilon=14\ 817$)

EXAMPLE 19

R,S-2-(E)-Phenylmethylene-1-(E)-{3-[bis(1-methylethyl)-amino]-2-hydroxy-propoxyimino}-cyclooctane a) The process of Example 18/a is followed.

b) The process of Example 1/b is followed.

Yield: 30.2 g (78%).

(E)-2-Butenedioate (1/1) Melting point: 105°–9° C.

Analysis for formula $C_{28}H_{42}N_2O_6$ (502.64): Calculated: C=66.90%; H=8.42%; N=5.57%; Found: C=67.18%; H=8.59%; N=5.61%.

UV: $\lambda_{max}=271$ nm ($\epsilon=13\ 395$)

EXAMPLE 20

R,S-2-(E)-Phenylmethylene-1-(E)-[3-(4-methyl-1-piperazinyl)-2-hydroxy-propoxyimino]-cyclooctane The process of Example 18 is followed except that 1-methyl-piperazine (11.0 g; 0.11 mole) is used instead of morpholine.

Yield: 33.1 g (86%).

(E)-2-Butenedioate (1/2) Melting point: 183°–8° C.

Analysis for formula $C_{31}H_{43}N_3O_{10}$ (617.67): Calculated: C=60.28%; H=7.02%; N=6.80%; Found: C=59.41%; H=7.14%; N=6.75%.

UV: $\lambda_{max}=269$ nm ($\epsilon=15\ 357$)

EXAMPLE 21

R,S-2-(E)-Phenylmethylene-{3-[bis-(1-methylethyl)-amino]-2-hydroxy-propoxyimino}-cyclopentane a) 2-(E)-Phenylmethylene-cyclopentane-1-one(E)-oxime (18.62 g; 0.1 mole) is transformed into a salt in a concentrated (30 to 40% by weight) alkali metal hydroxide (sodium and/or potassium hydroxide in water) solution in the presence of dimethyl sulfoxide. The salt thus obtained is reacted with 1-chloro-2,3-epoxypropane (13.88 g; 0.15 mole) at a temperature of 40° C. Further on the process of Example 1/a is followed.

Yield: 23.5 g (89.5%).

b) The process of Example 1/b is followed.

Yield: 28.0 g (82%).

(E)-2-Butenedioate (1/1) Melting point: 136°–8° C.

Analysis for formula $C_{25}H_{36}N_2O_6$ (458.53): Calculated: C=65.48%; H=7.91%; N=6.11%; Found: C=64.90%; H=7.76%; N=6.23%.

UV: $\lambda_{max}=299$ nm ($\epsilon=23\ 264$)

EXAMPLE 22

R,S-2-(E)-Phenylmethylene-1-(E)-[3-(1,1-dimethylethylamino)-2-hydroxy-propoxyimino]-cyclopentane The process of Example 21 is followed except that 2-amino-2-methyl-propane (8.05 g; 0.11 mole) is used instead of diisopropyl amine.

Yield: 27.5 g (87%).

(E)-2-Butenedioate (1/2) Melting point: 178°–82° C.

Analysis for formula $C_{23}H_{32}N_2O_6$ (432.37): Calculated: C=63.89%; H=7.46%; N=6.48%; Found: C=64.41%; H=7.58%; N=6.60%.

UV: $\lambda_{max1}=303$ nm ($\epsilon=23\ 449$), $\lambda_{max2}=303$ nm ($\epsilon=23\ 893$)

EXAMPLE 23

R,S-(E)-(2-Chlorophenyl-methylene)-1-(E)-[3-(1,1-dimethylethylamino)-2-hydroxy-propoxyimino]-cyclohexane a) The process of Example 1/a is followed except that 2-(E)-(2-chlorophenyl-methylene)-cyclohexan-1-one-(E)-oxime (23.57 g; 0.1 mole) is used instead of 2-(E)-phenylmethylene-cyclohexan-1-one-(E)-oxime.

Yield: 29.3 g yellow oil (95.9%)

b) The process of Example 2/b is followed.

Yield: 31.4 g (86%)

(E)-2-Butenedioate (2/1) Melting point: 187°–91° C.

Analysis for formula $C_{22}H_{36}ClN_2O_4$ (427.99): Calculated: C=62.47%; H=7.38%; N=6.62%; Cl=8.38% Found: C=62.60%; H=7.52%; N=6.63%; Cl=8.52%.

EXAMPLE 24

R,S-2-(E)-Chlorophenylmethylene-1-(E)-[3-(4-phenyl-1-piperazinyl)-2-hydroxy-propoxyimino]-cyclohexane a) The process of Example 23/a is followed.

b) The process of Example 5/b is followed.

Yield: 39.0 g (86%)

(E)-2-Butenedioate (2/1) Melting point: 144°–46° C.

Analysis for formula $C_{28}H_{34}ClN_3O_4$ (512.03): Calculated: C=65.68%; H=6.69%; N=8.21%; Cl=6.92%; Found: C=65.70%; H=6.79%; N=8.26%; Cl=6.85%

UV: $\lambda_{max}=247$ nm ($\epsilon=20\ 610$)

EXAMPLE 25

R,S-2-(E)-3-Chlorophenylmethylene-1-(E)-[3-(2-methylpropyl-amino)-2-hydroxy-propoxyimino]-cyclohexane a) The process of Example 23/a is followed except that 2-(E)-(2-chlorophenyl-methylene)-cyclohexan-1-one-(E)-oxime is used instead of 2-(E)-(2-chlorophenyl-methylene)-cyclohexan-1-one-(E)-oxime.

Yield: 29.5 g (93.5%)

b) The process of Example 1/b is followed except that 1-amino-2-methyl-propane (8.05 g; 0.11 mole) is used instead of diisopropyl amine.

(E)-2-Butenedioate (2/1) Melting point: 158°–63° C.
Analysis for formula $C_{22}H_{31}ClN_2O_4$ (422.95): Calculated: C=62.47%; H=7.39%; N=6.63%; Cl=8.38%; Found: C=62.58%; H=7.35%; N=6.58%; Cl=8.30%.

UV: $\lambda_{max}$=278 nm ($\epsilon$=14 805)

EXAMPLE 26

R,S-2-(E)-(4-Chlorophenyl-methylene)-1-(E)-[3-(1-methylethylamino)-2'-hydroxy-propoxyimino]-cyclohexane a) The process of Example 25/a is followed.

b) The process of Example 1/b is followed except that 2-aminopropanol (6.5 g; 0.11 mole) is used instead of diisopropyl amine.

Yield: 27.0 g (77%).

(E)-2-Butenedioate (2/1) Melting point: 126°–30° C.
Analysis for formula $C_{21}H_{29}ClN_2O_4$ (408.92): Calc.: C=61.69%; H=7.15%; N=6.85%; Cl=8.68%; Found: C=61.68%; H=7.19%; N=7.00%; Cl=8.62%.

UV: $\lambda_{max}$=277 nm ($\epsilon$=14 920)

EXAMPLE 27

R,S-2-(E)-(4-Chlorophenyl-methylene)-1-(E)-(3-cyclopropylamino-2-hydroxy-propoxyimino)-cyclohexane a) 2(E)-(4-Chlorophenyl-methylene)-cyclohexan-1-one-(E)-oxime (23.57 g; 0.1 mole) is transformed into a salt with the aid of sodium amide (3.9 g; 0.1 mole in the form of 50% by weight toluene suspension) in a mixture of dimethyl formamide and toluene. Further on the process of Example 1/a is followed.

Yield: 29.2 g (95.9%)

b) The process of Example 1/b is followed except that cyclopropyl amine (6.28 g; 0.11 mole) is used instead of diisopropyl amine.

Yield: 28.3 g (81%)

(E)-2-Butenedioate (2/1) Melting point: 156°–60° C.
Analysis for formula $C_{21}H_{27}ClN_2O_4$ (406.91): Calc.: C=61.98%; H=6.69%; N=6.89%; Cl=8.71; Found: C=62.11%; H=6.83%; N=6.86%; Cl=8.70.

UV: $\lambda_{max}$=280 nm ($\epsilon$=37 645)

EXAMPLE 28

R,S-2-(E)-(4-Chlorophenyl-methylene)-1-(E)-[3-(1-methylethylamino)-2-hydroxy-propoxyimino]-cyclohexane 2-(E)-(4-Chlorophenyl-methylene)-cyclohexan-1-one-(E)-oxime (23.57 g; 0.1 mole) is reacted with 1-chloro-2-hydroxy-3-(1-methylethyl)-amino-propane in the presence of sodium ethylate (0.1 mole) in ethyl alcohol at the boiling temperature of the reaction mixture. The recovery of the product is carried out according to Example 1/b.

Yield: 12.64 g (36%)

(E)-2-Butenedioate (2/1) Melting point: 155°–9° C.
Analysis for formula $C_{21}H_{39}ClN_2O_4$ (418.99): Calc.: C=61.68%; H=7.15%; N=6.85%; Cl=8.67%; Found: C=62.02% 5 H=7.27%; N=6.91%; Cl=8.54%.

UV: $\lambda_{max}$=$2^{68}$ nm ($\epsilon$=37 859)

EXAMPLE 29

R,S-2-(E)-(4-Chlorophenyl-methylene)-1-(E)-(3-butylamino-2-hydroxy-propoxyimino)-cyclohexane a) The process of Example 27/a is followed.

b) The process of Example 1/b is followed except that n-butylamine (8.05 g; 0.11 mole) is used instead of diisopropyl amine.

Yield: 29.2 g (80%).

(E)-2-Butenedioate (2/1) Melting point: 133°–7° C.
Analysis for formula $C_{24}H_{33}ClN_2O_6$ (488.08): Calc.: C=59.92%; H=6.92%; N=5.82%; Cl=7.37%; Found: C=59.88%; H=6.86%; N=5.86%; Cl=7.40%.

UV: $\lambda_{max}$=281 nm ($\epsilon$=19253)

EXAMPLE 30

R,S-2-(E)-(4-Chlorophenyl-methylene)-1-(E)-[3-(2-methylpropylamino)-2-hydroxy-propoxyimino]-cyclohexane a) The process of Example 27/a is followed.

b) The process of Example 25/b is followed.

Yield: 28.6 g (78%).

(E)-2-Butenedioate (2/1) Melting point: 157°–60° C.
Analysis for formula $C_{22}H_{31}ClN_2O_4$ (422.95): Calc.: C=62.47%; H=7.39%; N=6.62%; Cl=8.38%; Found: C=62.28%; H=7.47%; N=6.75%; Cl=8.53%.

UV: $\lambda_{max}$=280 nm ($\epsilon$=37 843)

EXAMPLE 31

R,S-2-(E)-(4-Chlorophenyl-methylene)-1-(E)-[3-(1,1-dimethylethylamino)-2'-hydroxy-propoxyimino]-cyclohexane 2-(E)-(4-Chlorophenyl-methylene)-cyclohexan-1-one (21.77 g; 0.1 mole) and 0-{[3-(1,1-dimethylethyl-amino)-2-hydroxy]-propyl-}hydroxylamine (14.82 g; 0.1 mole) dissolved in ethanol is reacted at the boiling temperature of the reaction mixture until the starting material cannot be detected any more by thin-layer chromatography (Kieselgel 60 $F_{254}$; eluent: a 4:1 mixture of benzene:methanol). To the reaction mixture fumaric acid (5.8 g; 0.05 mole) is added and the precipitated crystals are filtered off.

(E)-2-Butenedioate (2/1) Melting point: 182°–90° C.
Analysis for formula $C_{22}H_{31}ClN_2O_4$ (180.91): Calculated: C=62.47%; H=7.39%; N=6.62%; Cl=8.38%; Found: C=62.44%; H=7.37%; N=6.67%; Cl=8.33%.

UV: $\lambda_{max}$=278 nm ($\epsilon$=37 639)

EXAMPLE 32

R,S-2-(E)-(4-Chlorophenyl-methylene)-1-(E)-[3-(1,1-dimethylpropin-2-yl-amino)-2-hydroxy-propoxyimino]-cyclohexane a) 2-(E)-(4-Chlorophenyl-methylene)-cyclohexan-1-one-(E)-oxime (23.57 g; 0.1 mole) is reacted with sodium hydride (4.8 g; 0.1 mole in the form of a 50% by weight oily suspension) in a mixture of benzene and dimethyl formamide in order to obtain a salt. The salt thus obtained is reacted with 1-(mezyloxy)-2,3-epoxypropane (15.17 g; 0.1 mole) at a temperature of 40° to 50° C. Further on the process of Example 1/a is followed.

Yield: 28.8 g (91.6%) brown oil b) The process of 1/b is followed except that 1,1-dimethyl-propin-2-yl-amine (9.14 g; 0.11 mole) is used instead of diisopropyl amine.

Yield: 31.1 g (83%)

(E)-2-Butenedioate (1/1) Melting point: 148°–54° C.

Analysis for formula $C_{25}H_{31}ClN_2O_4$ (491.0): Calc.: C=61.15%; H=6.36%; N=5.71%; Cl=7.22%; Found: C=61.41%; H=6.41%; N=5.64%; Cl=7.18%.

UV: $\lambda_{max}=278$ nm ($\epsilon=21\ 480$)

EXAMPLE 33

R,S-2-(E)-(3,4-Dichlorophenyl-methyl)-1-(E)-(3-butylamino-2-hydroxy-propoxyimino)-cyclohexane a) The process of Example 1/a is followed except that 2-(E)-(3,4-Dichlorophenyl-methylene)-cyclohexan-1-one-(E)-oxime (27.02 g; 0.1 mole) is used instead of 2-(E)-phenylmethylene-cyclohexan-1-one-(E)-oxime.

Yield: 31.5 g (90.2%)

b) The process of Example 29/b is followed.

Yield: 30.4 g (76%)

(E)-2-Butenedioate (2/1) Melting point: 138°–43° C.

Analysis for formula $C_{22}H_{30}Cl_2N_2O_4$ (457.38): Calc.: C=57.77%; H=6.61%; N=6.13%; Cl=15.50%; Found: C=57.97%; H=6.61%; N=6.24%; Cl=15.58%.

UV: $\lambda_{max}=275$ nm ($\epsilon=15\ 150$)

EXAMPLE 34

R,S-2-(E)-(3,4-Dichlorophenyl-methylene)-1-(E)-(3-/bis-n-propyl/-amino-2-hydroxy-propoxyimino)-cyclohexane a) The process of Example 33/a is followed.

b) The process of Example 1/b is followed except that dipropyl amine (11.13 g; 0.11 mole) is used instead of diisopropyl amine.

Yield: 29.5 g (80%).

Analysis for formula $C_{24}H_{34}Cl_2N_2O_4$ (485.4): Calc.: C=59.38%; H=7.06%; N=5.77%; Cl=14.61%; Found: C=59.05%; H=6.97%; N=5.78%; Cl=14.35%.

UV: $\lambda_{max}=280$ nm ($\epsilon=12\ 494$)

EXAMPLE 35

R,S-2-(E)-(2,6-Dichlorophenyl-methylene)-1-(E)-(3-propylamino-2-hydroxy-propoxyimino)-cyclohexane a) The process of Example 1/a is followed except that 2-(E)-(2,6-diChlorophenyl-methylene)-cyclohexan-1-one-(E)-oxime (27.02 g; 0.1 mole) is used instead of 2-(E)-phenylmethylene-cyclohexan-1-one-(E)-oxime.

Yield: 33.3 g (95.1%)

b) The process of Example 1/b is followed except that n-propyl amine (6.5 g; 0.11 mole) is used instead of diisopropyl amine.

Yield: 32.8 g (85%).

(E)-2-Butenedioate (2/1) Melting point: 170°–3° C.

Analysis for formula $C_{21}H_{28}Cl_2N_2O_4$ (443.37): Calc.: C=56.88%; H=6.36%; N=6.32%; Cl=16.0%; Found: C=56.85%; H=6.34%; N=6.29%; Cl=16.14%.

UV: $\lambda_{max}=259$ nm ($\epsilon=10\ 357$)

EXAMPLE 36

R,S-2-(E)-(2,6-Dichlorophenyl-methylene)-1-(E)-[3-(4-methyl-1-piperazinyl)-2-hydroxy-propoxyimino]-cyclohexane The process of Example 35 is followed except that 1-methyl-piperazine (11.0 g; 0.11 mole) is used instead of n-propyl amine.

Yield: 39.2 g (92%)

(E)-2-Butenedioate (2/1) Melting point: 182°–7° C.

Analysis for formula $C_{29}H_{37}Cl_2N_3O_{10}$ (658.51): Calc.: C=52.89%; H=5.66%; N=6.38%; Cl=10.77%; Found: C=52.18%; H=5.57%; N=6.47%; Cl=10.75%.

UV: $\lambda_{max}=249$ nm ($\epsilon=12\ 719$)

EXAMPLE 37

R,S-2-(E)-(2-Methoxyphenyl-methylene)-1-(E)-(3-morpholinyl-2-hydroxy-propoxyimino)-cyclohexane a) The process of Example 1/a is followed except that 2-(E)-(2-methoxyphenyl-methylene)-cyclohexan-1-one-(E)-oxime (23.13 g; 0.1 mole) is used instead of 2-(E)-phenylmethylene-cyclohexan-1-one-(E)-oxime.

Yield: 29.7 g (95.3%)

b) The process of Example 15/b is followed.

Yield: 33.0 g (88%)

(E)-2-Butenedioate (2/3) Melting point: 158°–61° C.

Analysis for formula $C_{17}H_{36}N_2O_6$ (548.58): Calculated: C=59.11%; H=6.61%; N=5.11%; Found: C=59.22%; H=6.66%; N=5.20%.

UV: $\lambda_{max}=265$ nm ($\epsilon=12\ 523$)

EXAMPLE 38

R,S-2-(E)-(2-Methoxyphenyl-methylene)-1-(E)-{[4-(2-methoxyphenyl)-1-piperazinyl]-2-hydroxy-propoxyimino}-cyclohexane a) The process of Example 37/a is followed.

b) The process of Example 1/b is followed except that 1-(2-methoxyphenyl)-piperazine (21.15 g; 0.11 mole) is used instead of diisopropyl amine.

Yield: 43.6 g (91%)

Hydrochloride (1/1) Melting point: 105°–113° C.

Analysis for formula $C_{28}H_{38}ClN_3O_4$ (516.09): Calc.: C=65.16%; H=7.42%; N=8.15%; Cl=6.87%; Found: C=64.48%; H=7.37%; N=7.99%; Cl=6.97%.

UV: $\lambda_{max}=268$ nm ($\epsilon=12\ 941$)

EXAMPLE 39

R,S-2-(E)-(3-Methoxyphenyl-methylene)-1-(E)-{3-[(4-phenylmethyl)-1-piperazinyl]-2-hydroxy-propoxyimino}-cyclohexane a) The process of Example 37/a is followed except that 2-(E)-(3-methoxyphenyl-methylene)-cyclohexan-1-one-(E)-oxime is used instead of 2-(E)-(2-methoxyphenyl-methylene)-cyclohexan-1-one-(E)-oxime.

Yield: 29.1 g (96.2%)

b) The process of Example 6/b is followed.

Yield: 41.3 g (89%)

(Z)-2-Butenedioate (1/2) Melting point: 177°–80° C.

Analysis for formula $C_{36}H_{45}N_3O_{11}$ (695.74): Calculated: C=62.14%; H=6.52%; N=6.04%; Found: C=62.55%; H=6.55%; N=6.00%.

UV: $\lambda_{max1}=272$ nm ($\epsilon=14\ 952$),
$\lambda_{max2}=272$ nm ($\epsilon=14\ 922$)

Ethanedioate (1/2) Melting point: 190°–5° C.

Analysis for formula $C_{32}H_{41}N_3O_{11}$ (643.67): Calculated: C=59.80%; H=6.42%; N=6.53%; Found: C=59.88%; H=6.39%; N=6.55%.

Propanedioate (1/2) Melting point: 96°–100° C.
Analysis for formula $C_{34}H_{45}N_3O_{11}$ (671.72): Calculated: C=60.79%; H=6.75%; N=6.26%; Found: C=60.55%; H=6.77%; N=6.33%.

(E)-2-Butenedioate (1/2) Melting point: 176°–80° C.
Analysis for formula $C_{36}H_{45}N_3O_{11}$ (695.74): Calculated: C=62.14%; H=6.52%; N=6.04%; Found: C=62.15%; H=6.64%; N=6.13%.

EXAMPLE 40

R,S-2-(E)-(4-Methoxyphenyl-methylene)-1-(E)-(3-cyclopropylamino-2-hydroxy-propoxyimino)-cyclohexane a) The process of Example 37/a is followed except that 2-(E)-(4-methoxyphenyl-methylene)-cyclohexan-1-one-(E)-oxime is used instead of 2-(E)-(2-methoxyphenyl-methylene)-cyclohexan-1-one-(E)-oxime.
Yield: 30.1 g (98.7%)
b) The process of Example 28/b is followed.
Yield: 30.1 g (83%)
(E)-2-Butenedioate (2/1) Melting point: 165°–7° C.
Analysis for formula $C_{22}H_{30}N_2O_5$ (402.48): Calculated: C=65.64%; H=7.51%; N=6.96%; Found: C=64.97%; H=7.39%; N=6.86%.
UV: $\lambda_{max}=288$ nm ($\epsilon=18\ 789$)

EXAMPLE 41

R,S-2-(E)-(4-Methoxyphenyl-methylene)-1-(E)-[3-(3-dimethylamino-1-propylamino)-2-hydroxy-propoxyimino]-cyclohexane a) The process of Example 40 is followed except that 3-dimethylamino-1-propylamine (11.24 g; 0.11 mole) is used instead of cyclopropyl amine.
Yield: 30.4 g (78%)
(E)-2-Butenedioate (1/2) Melting point: 170°–2° C.
Analysis for formula $C_{30}H_{43}N_3O_{11}$ (621.66): Calculated: C=57.96%; H=6.97%; N=6.76%; Found: C=58.07%; H=7.00%; N=6.85%.
UV: $\lambda_{max}=160$ nm ($\epsilon=19\ 486$)

EXAMPLE 42

R,S-2-(E)-(4-Methoxyphenyl-methylene)-1-(E)-(3-cyclopropylamino-2-hydroxy-propoxyimino)-cycloheptane a) The process of Example 1/a is followed except that 2-(E)-(4-methoxyphenyl-methylene)-cycloheptan-1-one-(E)-oxime (24.53 g; 0.1 mole) is used instead of 2-(E)-phenylmethylene-cyclohexan-1-one-(E)-oxime.
Yield: 30.5 g (96.1 g)
b) The process of Example 27/b is followed.
Yield: 30.8 g (86%)
(E)-2-Butenedioate (2/1) Melting point: 155°–8° C.
Analysis for formula $C_{23}H_{32}N_2O_5$ (416.5): Calculated: C=66.32%; H=7.69%; N=6.73%; Found: C=66.09%; H=7.61%; N=6.80%. UV: $\lambda_{max}=276$ nm ($\epsilon=19\ 887$)

EXAMPLE 43

R,S-2-(E)-(4'-Methoxyphenyl-methylene)-1-(E)-(3-propylamino-2-hydroxy-propoxyimino)-cycloheptane a) The process of Example 42/a is followed.
b) The process of Example 35/b is followed.
Yield: 29.6 g (82%)
(E)-2-Butenedioate (2/1) Melting point: 163°–6° C.
Analysis for formula $C_{23}H_{34}N_2O_5$ (418.5): Calculated: C=66.0%; H=8.19%; N=6.70%; Found: C=65.76%; H=8.22%; N=6.80%.
UV: $\lambda_{max}=276$ nm ($\epsilon=16\ 659$)

EXAMPLE 44

R,S-2-(E)-(4-Methoxyphenyl-methylene)-1-(E)-(3-diethylamino-2-hydroxy-propoxyimino)-cycloheptane a) The process of Example 42/a is followed.
b) The process of Example 1/b is followed except that diethyl amine (8.05 g; 0.11 mole) is used instead of diisopropyl amine.
Yield: 27.0 g (72%)
(E)-2-Butenedioate (2/1) Melting point: 121°–3° C.
Analysis for formula $C_{24}H_{36}N_2O_5$ (432.55): Calculated: C=66.64%; H=8.39%; N=6.48%; Found: C=66.78%; H=8.24%; N=6.51%.
UV: $\lambda_{max}=273$ nm ($\epsilon=19220$)

EXAMPLE 45

R,S-2-(E)-(4-Chlorophenyl-methylene)-1-(E)-[3'-(N-methyl-N-cyclohexylamino)-2-hydroxy-propoxyimino]-cyclohexane a) The process of Example 27/a is followed.
b) The process of example 27/b is followed except that N-methyl-N-cyclohexyl amine (12.45 g; 0.11 mole) is used instead of cyclopropyl amine.
Yield: 34.4 g (85%)
(E)-2-Butenedioate (1/1) Melting point: 155°–60° C.
Analysis for formula $C_{22}H_{37}ClN_2O_6$(521.05): Calculated: C=62.23%; H=7.16%; N=5.38%; Cl=6.80%; Found: C=62.57%; H=7.02%; N=5.47%; Cl=6.83%.
UV: $\lambda_{max}=276$ nm ($\epsilon=18\ 423$)

EXAMPLE 46

R,S-2-(E)-(4-Chlorophenyl-methylene)-1-(E)-(3-propylamino-2-hydroxypropoxyimino)-cyclohexane a) The process of Example 27/a is followed.
b) The process of Example 1/b is followed except that n-propyl amine (6.28 g; 0.11 mole) is used instead of diisopropyl amine.
Yield: 28.3 g (81%)
(E)-2-Butenedioate (2/1) Melting point: 145°–47° C.
Analysis for formula $C_{21}H_{27}ClN_2O_4$ (406.91): Calc.: C=61.98%; H=6.69%; N=6.89%; Cl=8.71%; Found: C=61.95%; H=6.75%; N=6.91%; Cl=8.61%.
UV: $\lambda_{max}=276$ nm ($\epsilon=18\ 669$)

EXAMPLE 47

R,S-2-(E)-(4-Chlorophenyl-methyl)-1-(E)-[3-(1-methylethyl-amino)-2-hydroxy-propoxyimino]-cyclohexane a) The process of Example 1/a is followed except that 2-(E) -(4-chlorophenyl-methyl)-cyclohexan-1-one-(E)-oxime (23.77 g; 0.1 mole) is used instead of 2-(E)-phenylmethylene-cyclohexan-1-one-(E)-oxime.
Yield: 29.5 g (94.2%)
b) The process of Example 26/b is followed.
Yield: 29.3 g (82%)
(E)-2-Butenedioate (2/1) Melting point: 140°–45° C.
Analysis for formula $C_{21}H_{31}ClN_2O_4$ (410.94): Calc.: C=61.37%; H=7.60%; N=6.82%; Cl=8.63%; Found: C=61.73%; H=7.59%; N=6.87%; Cl=8.79%.
UV: $\lambda_{max1}=266$ nm ($\epsilon=6\ 030$)
$\lambda_{max2}=272$ nm ($\epsilon=5\ 072$)

EXAMPLE 48

R,S-2-(E)-Phenylmethylene-1-(E)-[3-(1-methylethylamino)-2-hydroxypropxyimino]-cyclooctane a) The process of Example 18/a is followed.
b) The process of Example 26/b is followed.
Yield: 29.9 g (86%)
(E)-2-Butenedioate (1/1) Melting point: 158°-60° C.
Analysis for formula $C_{25}H_{36}N_2O_6$ (418.52): Calculated: C=65.19%; H=7.88%; N=6.08%; Found: C=64.79%; H=7.77%; N=5.98%.
UV: $\lambda_{max}$=270 nm ($\epsilon$=13 535)

EXAMPLE 49

R,S-2-(E)-Phenylmethylene-1-(E)-(3-butylamino-2-hydroxypropoxyimino)-cyclooctane a) The process of Example 18/a is followed.
b) The process of Example 29/b is followed.
Yield: 29.1 g (81%)
(E)-2-Butenedioate (2/1) Melting point: 161°-2° C.
Analysis for formula $C_{24}H_{36}N_2O_4$ (416.55): Calculated: C=69.20%; H=8.71%; N=6.73%; Found: C=68.45%; H=8.51%; N=6.81%.
UV: $\lambda_{max}$=272 nm ($\epsilon$=13 744)

EXAMPLE 50

R,S-2-(E)-(4-Methoxyphenyl-methylene)-1-(E)-/3-(1-methylethylamino)-2-hydroxy-propoxyimino/-cycloheptane a) The process of Example 42/a is followed.
b) The process of Example 26/b is followed.
Yield: 29.4 g (82%)
(E)-2-Butenedioate (2/1) Melting point: 181°-3° C.
Analysis for formula $C_{23}H_{34}N_2O_5$ (418.5): Calculated: C=66.00%; H=8.19%; N=6.69%; Found: C=65.55%; H=8.08%; N=6.76%.
UV: $\lambda_{max}$=274 nm ($\epsilon$=18 044)

EXAMPLE 51

R,S-2-(E)-(4-Methoxyphenyl-methylene)-1-(E)-(3-dipropylamino-2-hydroxy-propoxyimino)-cycloheptane a) The process of Example 42/a is followed.
b) The process of Example 34/b is followed.
Yield: 34.0 g (85%)
(E)-2-Butenedioate (2/1) Melting point: 84°-87° C.
Analysis for formula $C_{26}H_{40}N_2O_5$ (460.6): Calculated: C=67.79%; H=8.75%; N=6.08%; Found: C=67.34%; H=8.77%; N=6.02%.
UV: $\lambda_{max}$=272 nm ($\epsilon$=18 458)

EXAMPLE 52

R,S-2-(E)-Phenylmethylene-1-(E)-{3-[4-(3-chlorophenyl)-1-piperazinyl]-2-hydroxy-propoxyimino}-cyclohexane The process of Example 1 is followed except that 1-(3-chlorophenyl)-piperazine (21.63 g; 0.11 mole) is used instead of diisopropyl amine.
Yield: 41.3 g (91%)
Hydrochloride (1/1) Melting point: 164°-8° C.
Analysis for formula $C_{26}H_{33}Cl_2N_3O_2$ (490.45): Calculated: C=63.67%; H=6.78%; N=8.57%; Cl=14.46%; Found: C=62.45%; H=6.90%; N=8.43%; Cl=14.46%.
UV: $\lambda_{max1}$=249 nm ($\epsilon$=20 874),
$\lambda_{max2}$=272 nm ($\epsilon$=16 797)

EXAMPLE 53

R,S-2-(E)-Phenylmethylene-1-(E)-3-[4-(3-trifluoromethyl)-phenyl-1-piperazinyl]-2-hydroxy-propoxyiminocyclohexane The process of Example 1 is followed except that 1-(3-trifluoromethyl)-phenyl piperazine (25.3 g; 0.11 mole) is used instead of diisopropyl amine.
Yield: 46.3 g (95%).
(E)-2-Butenedioate (2/1) Melting point: 162°-65° C.
Analysis for formula $C_{29}H_{34}F_3N_3O_4$ (545.58): Calculated: C=63.84%; H=6.28%; N=7.70%; F=10.45%; Found: C=63.71%; H=6.23%; N=7.62%; F=10.33%.
UV: $\lambda_{max}$=257 nm ($\epsilon$=23 003)

EXAMPLE 54

R,S-2-(E)-Phenylmethylene-1-(E)-[3-(4-phenylmethyl)-1-piperidinyl)-2-hydroxy-propoxyimino]-cyclohexane The process of Example 1 is followed except that 1-phenylmethyl piperidine (19.3 g; 0.11 mole) is used instead of diisopropyl amine.
Yield: 38.0 g (88%)
(E)-2-Butenedioate (1/1) Melting point: 157°-61° C.
Analysis for formula $C_{30}H_{38}N_2O_4$ (490.63): Calculated: C=73.44%; H=7.81%; N=5.71%; Found: C=72.92%; H=7.93%; N=5.62%.
UV: $\lambda_{max}$=272 nm ($\epsilon$=15 210)

EXAMPLE 55

R,S-2-(E)-Phenylmethylene-1-(E)-[3-(4-phenyl-1,2,3,6-tetrahydro)-1-pyridinyl]-2-hydroxy-propoxyiminocyclohexane The process of Example 1 is followed except that 4-phenyl-1,2,3,6-tetrahydropyridine (17.5 g; 0.11 mole) is used instead of diisopropyl amine. Yield: 32.4 g (77.0%).
(E)-2-Butenedioate (2/1) Melting point: 149°-50° C.
Analysis for formula $C_{29}H_{34}N_3O_4$ (474.61): Calculated: C: 73.23%; H: 7.22%; N: 5.89%; Found: C: 73.64%; H: 7.44%; N: 5.78.
UV: $\lambda_{max}$=248 ($\epsilon$=20 582)

EXAMPLE 56

Tablet comprising 25 mg of active ingredient
Composition of one tablet is as follows:

| | |
|---|---|
| active ingredient | 25.0 mg |
| corn starch | 97.0 mg |
| polyvinyl-pyrrolidone | 175.0 mg |
| magnesium stearate | 3.0 mg |
| | 300.0 mg |

The tablet is prepared as follows:
The active ingredient and the corn starch are admixed, then wetted with 10-15% by weight of aqueous polyvinylpyrrolidone solution and the mixture is granulated then dried at a temperature of 40° to 50° C. The dry granules is rubbed through a sieve, mixed with talcum and magnesium stearate and tablets are prepared from the mixture.
The weight of one tablet is 300.0 mg.

EXAMPLE 57

Tablet comprising 250 mg of active ingredient
The composition of one tablet is as follows:

| | |
|---|---|
| active ingredient | 250.0 mg |
| lactose | 270.0 mg |
| corn starch | 75.0 mg |
| magnesium stearate | 5.0 mg |

The active ingredient, lactose and corn starch are wetted and mixed, granulated and dried at a temperature of 40° to 50° C. The dry granules are rubbed through a sieve as described hereinabove, mixed with magnesium stearate and talcum, then tablets are formed. The weight of one tablet is 600.0 mg.

EXAMPLE 58

Dragee comprising 25 mg of active ingredient
The composition of one dragee core is as follows:

| | |
|---|---|
| active ingredient | 25.0 mg |
| corn starch | 245.0 mg |
| talcum | 18.0 mg |
| gelatine | 8.0 mg |
| magnesium stearate | 4.0 mg |

The active ingredient and corn starch are mixed, wetted with 10% by weight aqueous gelatine solution, granules are formed from the wet mixture, then the granules are dried at a temperature of 40° to 50° C. The dry granules are rubbed through a sieve, homogenized with talcum and magnesium stearate and dragee cores of 300.0 mg are compressed from the mixture.

EXAMPLE 59

Dragee comprising 50.0 mg of active ingredient
The composition of one dragee core is as follows:

| | |
|---|---|
| active ingredient | 50.0 mg |
| lactose | 97.0 mg |
| polyvinyl-pyrrolidone | 2.0 mg |
| magnesium stearate | 1.0 mg |

The granules are prepared as described hereinabove. The weight of the dragee cores is 150.0 mg.

The dragee cores are coated with a layer containing sugar and talcum in a manner known per se. The dragee thus obtained is painted with non-toxic food paint to the desired colour and polished with bee-wax.

EXAMPLE 60

Gelatine capsule comprising 5.0 mg of active ingredient
The composition of one gelatine capsule is as follows:

| | |
|---|---|
| active ingredient | 5.0 mg |
| corn starch | 40.0 mg |
| Aerosil | 3.0 mg |
| magnesium stearate | 2.0 mg |

The ingredients are homogenized and filled into gelatine capsules of suitable size.

EXAMPLE 61

Gelatine capsule comprising 25.0 mg of active ingredient
The composition of one gelatine capsule is as follows:

| | |
|---|---|
| active ingredient | 25.0 mg |
| corn starch | 265.0 mg |
| Aerosil | 6.0 mg |
| magnesium stearate | 4.0 mg |

The ingredients are homogenized and filled into gelatine capsules of suitable size.

EXAMPLE 62

Gelatine capsule comprising 50.0 mg of active ingredient
The composition of one gelatine capsule is as follows:

| | |
|---|---|
| active ingredient | 50.0 mg |
| lactose | 90.0 mg |
| Aerosil | 6.0 mg |
| magnesium stearate | 4.0 mg |

The ingredients are homogenized and filled into gelatine capsules of suitable size.

EXAMPLE 63

Gelatine capsule comprising 250.0 mg of active ingredient
The composition of one gelatine capsule is as follows:

| | |
|---|---|
| active ingredient | 250.0 mg |
| lactose | 148.0 mg |
| magnesium stearate | 2.0 mg |

The ingredients are homogenized and filled into gelatine capsules of suitable size.

EXAMPLE 64

Injection comprising 25.0 mg of active ingredient
The composition of one ampoule is as follows:

| | |
|---|---|
| active ingredient | 25.0 mg |
| sodium chloride | 5.0 mg | dissolved in 5 ml of twice-distilled water.

The active ingredient and sodium chloride are dissolved in the necessary amount of twice-distilled water suitable for making injections. The solution is filtered, filled into ampoules and sterilized.

EXAMPLE 65

Injection comprising 50.0 mg of active ingredient
The composition of one ampoule is as follows:

| | |
|---|---|
| active ingredient | 50.0 mg |
| sodium chloride | 10.0 mg |

The active ingredient and sodium chloride are dissolved in the necessary amount of twice-distilled water, then filled into ampoules under sterile conditions.

EXAMPLE 66

Suppository comprising 250 mg of active ingredient
The composition of one suppository is as follows:

| | |
|---|---|
| active ingredient | 250.0 mg |
| fatty acid glyceride | 750.0 mg |

The fatty acid glyceride is melted, the active ingredient is homogenized, then poured into a mould. One suppository weights 1000.0 mg and comprises 250.0 mg of active ingredient.

EXAMPLE 67

Drop comprising 5% by weight of active ingredient

| | |
|---|---|
| active ingredient | 50.0 mg |
| sorbitol | 340.0 mg |
| polyethylene glycol | 100.0 mg |
| citric acid | 1.0 mg |
| sodium citrate | 3.0 mg |
| ion-free water | 1.0 mg |
| flavourant | 1.0 mg |
| | 505.0 mg |

The sorbitol, the active ingredient, citric acid and sodium citrate are dissolved in the aqueous solution of propylene glycol, then after dissolution of the solid materials, the flavourant is added. The solution is filtered off and filled into flasks supplied with a drop-dispenser.

EXAMPLE 68

R,S-2-(E)-Phenylmethylene-1-(E)-{3-[bis-(1-methylethyl)-amino]-2-hydroxy-propoxyimino-cyclohexane a) To a flask of 250 ml volume supplied with a stirrer 40.3 g (0.2 mole) of 2-(E)-phenylmethylene-thiocyclohexanone, 100 ml of dry pyridine and 30.2 g (0.21 mole) of 3-amino-oxy-1,2-dihydroxypropane hydrochloride are added. The reaction is completed within 3 hours at a temperature of 25° C. under vigorous stirring. The end of the reaction is controlled by thin-layer chromatography (Kieselgel 60 $F_{254}$; eluent: a 8:1 mixture of benzene:methanol; development: UV light and iodine vapour). The reaction is continued until the starting material disappears.

At the end of the reaction pyridine is distilled off under reduced pressure, the residual red oil is diluted with 100 ml of benzene, washed with 5×30 ml of water, then the solvent is evaporated.

The residue is 52.3 g (95%) red oil of 2-(E)-phenylmethylene-1-(E)-(2',3'-dihydroxy-propoxyimino)-cyclohexane.

b) To a flask supplied with a stirrer 52.3 g (0.19 mole) of 2-(E)-phenylmethylene-1-(E)-(2',3'-dihydroxypropoxyimino)-cyclohexane, 20.2 g of triethyl amine and 200 ml of dichloro methane are fed, then a mixture of 14.6 ml of thionyl chloride and 20 ml of dichloro methane is added to the reaction mixture at a temperature of 0° C. The reaction mixture is stirred for further 30 minutes, the hydrochloric salt is filtered off and the solution is evaporated. 32.14 g (0.1 mole) of the 2-(E)-phenylmethylene-1-(L)-{[(1',2',3'-dioxathiolane-2'-oxide)-4'-yl]-methyloxy-imino}-cyclohexane thus obtained are boiled together with 40.4 g (0.4 mole) of diisopropyl amine and 150 ml of acetonitrile for 20 hours. The solution is evaporated under reduced pressure and the residue is recrystallized from n-hexane.

Yield: 28.4 g (79.3%) white crystal
Melting point: 47°–49.5° C.

EXAMPLE 69

R,S-2-(E)-Phenylmethylene-1-(E)-[3'-(4-morpholinyl)-2'-benzoyloxy-propoxyimino]-cyclooctane 37.25 g (0.1 mole) of R,S-2-(E)-phenylmethylene-1-(E)-[3'-(4-morpholinyl)-2'-hydroxy-propoxyimino]-cyclooctane are reacted with 22.62 g (0.1 mole) of benzoic acid anhydride in 400 ml of toluene at the boiling point of the reaction mixture. Then the reaction mixture is washed with diluted aqueous ammonium hydroxide solution, the toluene phase is dried over potassium carbonate and evaporated under reduced pressure.

Yield: 36.25 g (76.1%) yellow oil
The base is transformed into (E)-2-butenedioate salt.
(E)-2-Butenedioate Melting point: 155°–160°.C.

Analysis for formula $C_{33}H_{40}N_2O_8$ (592.7): Calc.: C=66.87%; H=6.80%; N=4.73%; Found: C=66.95%; H=6.82%; N=4.95%.

UV: $\lambda_{max}$=270 nm ($\epsilon$=15 110)

EXAMPLE 70

R,S-2-(E)-Phenylmethylene-1-(E)-{3'-[bis-(2''-methylethyl)-amino]-2'-benzoyloxy-propoxyimino}-cyclohexane 35.85 g (0.1 mole) of R,S-2-(E)-phenylmethylene-1-(E)-3'-[bis-(2''-methylethyl)-amino]-2'-hydroxy-propoxyimino-cyclo-hexane are reacted with 14.1 g (0.1 mole) of benzoyl chloride in the mixture of 500 ml of dichloromethane, 10.1 g (0.1 mole) of triethyl amine and 25 ml of dimethyl formamide at the boiling point of the reaction mixture for 10 hours.

Then the triethyl amine hydrochloride formed as a by-product is filtered off, the filtrate is washed with 3×20 ml of 5% by weight sodium hydroxide solution, dried over anhydrous magnesium sulfate and evaporated.

Yield: 38.6 g (82.8%) yellow oil
Analysis for formula $C_{29}H_{38}N_2O_3$ (462.6): Calculated: C=75.29%; H=8.28%; N=6.06%; Found: C=74.97%; H=8.31%; N=5.98%.

UV: $\lambda_{max1}$=222 nm ($\epsilon$=74 262), $\lambda_{max2}$=271 nm ($\epsilon$=60 097)

EXAMPLE 71

R,S-2-(E)-[3',4'-(Methylenedioxy)-phenylmethylene]-1-(E)-{3-[bis-(1-methylethyl)-amino]-2-hydroxy-propoxyimino}-cyclohexane The process of Example 1 is followed except that 2-(E)-[3',4'-(methylenedioxide)-phenylmethylene]-cyclohexane-1-one-(E)-oxime (24.5 g; 0.1 mole) is used instead of 2-(E)-phenylmethylene-cyclohexane-1-one-(E)-oxime.

(E)-2-Butenedioate (1/1) Melting point: 196° C.
Analysis for formula $C_{27}H_{38}N_2O_8$: Calculated: C=62.54%; H=7.39%; N=5.90%; Found: C=62.13%; H=7.30%; N=5.87%.

UV: $_{max}$=304 nm (=13 074)

EXAMPLE 72 a)

(+)-2-(E)-Phenylmethylene-1-(E)-{3-[bis-(1-methylethyl)-amino]-2-hydroxy-propoxyimino}-cyclohexane 71.7 g (0.2 mole) of (±)-2-(E)-phenylmethylene-1-(E)-3-[bis-(1-methylethyl)-amino]-2-hydroxy-propoxyimino}-cyclohexane (prepared according to Example 1/b) are dissolved in 1300 ml of methanol, then 71.6 g (0.2 mole) of (+)-dibenzoyl tartaric acid are added. After a few minute stirring the precipitation of crystals begins from the solution. The product is crystallized at a temperature of 5° C. and filtered off.

Yield: 70.8 g (98.8%) (+)-2-(E)-phenylmethylene-1-(E)-{3-[bis-(1-methylethyl)-amino]-2-hydroxy-propoxyimino}-cyclohexane (+)-dibenzoyl tartarate. Melting point: 185°-187° C.

The tartarate is treated with a calculated amount of 1N sodium hydroxide solution in a mixture of water and dichloroethane, the dichloroethane solution is separated and the solvent is evaporated. Thus (+)-2-(E)-phenylmethylene-1-(E)-{3-[bis-(1-methylethyl)-amino]-2-hydroxy-propoxyimino}-cyclohexane is obtained.

$[\alpha]_D^{20} = +2.5°$ (c=1; methanol)

Hydrochloride (1/1) Melting point: 195° C. (decomp.)

$[\alpha]_D^{20} = +32.5°$ (c=1; methanol)

Analysis for formula $C_{22}H_{33}ClN_2O_2$ (395.0): Calculated: C=66.90%; H=8.93%; N=6.93%; Cl=8.98%; Found: C=66.58%; H=8.76%; N=6.44%; Cl=8.95%.

(E)-2-Butenedioate (1/1) Melting point: 145°-147° C.

$[\alpha]_D^{20} = +29.2°$ (c=1; methanol)

Analysis for formula $C_{26}H_{38}N_2O_6$ (474.6): Calculated: C=65.79%; H=8.07%; N=5.90%; Found: C=65.83%; H=7.98%; N=5.85%.

UV: $\lambda_{max}=273$ nm ($\epsilon=14\ 377$)

b)

(−)-2-(E)-Phenylmethylene-1-(E)-{3-[bis-(1-methylethyl)-amino]-2-hydroxy-propoxyimino}-cyclohexane The process of Example 72/a is followed. The mother liquor obtained in the course of the filtration of the (+)-dibenzoyl tartarate salt is evaporated and the (−)-2-(E)-phenylmethylene-1-(E)-{3-[bis-(1-methylethyl)-amino]-2-hydroxy-propoxyimino}-cyclohexane is liberated as described hereinabove from the (−)-2-(E)-phenylmethylene-1-(E)-{3-[bis-(1-methylethyl)-amino]-2-hydroxy-propoxyimino{-cyclohexane-(+)-dibenzoyl tartarate thus obtained.

$[\alpha]_D^{20} = -2.5°$ (c=1; methanol)

Hydrochloride (1/1) Melting point: 194° C. (decomp.)

$[\alpha]_D^{20} = -32.4°$ (c=1; methanol)

Analysis for formula $C_{22}H_{25}ClN_2O_2$ (395,0): Calculated: C=66.90%; H=8.93%; N=6.39%; Cl=8.98%; Found: C=66.82%; H=8.97%; N=6.43%; Cl=8.87%.

(E)-2-Butenedioate (1/1) Melting point: 145°-47° C.

$[\alpha]_D^{20} = -29.4°$ (c=1; methanol)

Analysis for formula $C_{26}H_{38}N_2O_6$ (474.6): Calculated: C=65.79%; H=8.07%; N=5.90%; Found: C=65.62%; H=8.12%; N=5.93%.

EXAMPLE 73 a)

(−)-2-(E)-Phenylmethylene-1-(E)-{3-[bis-(1-methylethyl)-amino]-2-hydroxy-propoxyimino}-cyclohexane The racemic product prepared according to Example 1/b (71.7 g; 0.2 mole) is dissolved in dichloro ethane (200 ml), then water (200 ml) and (−)-dibenzoyl tartaric acid (35.8 g; 0.1 mole) are added. The reaction mixture is stirred at a temperature of 15° to 20° C. for 10 hours, and the product is filtered off.

Yield: 69.6 g (97.2%) of (−)-2-(E)-phenylmethylene-1-(E)-{3-[bis-(1-methylethyl)-amino]-2-hydroxy-propoxyimino}-cyclohexane-(−)-dibenzoyl tartarate.

(−)-2-(E)-Phenylmethylene-1-(E)-3-[bis-(1-methylethyl)-amino]-2-hydroxy-propoxyimino-cyclohexane $[\alpha]_D^{20} = -2.5°$ (c=1; methanol)

(E)-2-Butenedioate Melting point: 145°-147° C.

$[\alpha]_D^{20} = -28.9°$ (c=1; methanol)

b)

(+)-2-(E)-Phenylmethylene-1-(E)-{3-[bis-(1-methylethyl)-amino]-2-hydroxy-propoxyimino}-cyclohexane The dichloro ethane mother liquor obtained during the filtration of the (−)-dibenzoyl tartaric acid salt is evaporated after drying over anhydrous magnesium sulfate.

Yield: 34.9 g (97.4%) of (+)-2-(E)-phenylmethylene-1-(E)-{3-[bis-(1-methylethyl)-amino]-2-hydroxy-propoxyimino}-cyclohexane-(−)-dibenzoyl tartarate.

$[\alpha]_D^{20} = +2.5°$ (c=1; methanol)

Hydrochloride (1/1) Melting point: 194° C. (decomp.)

$[\alpha]_D^{20} = +32.4°$ (c=1; methanol)

We claim:

1. A racemic or optically active aminopropanol derivative of formula I

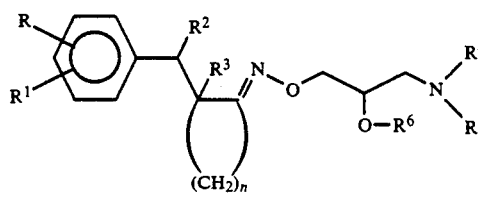

wherein

R and $R^1$ are independently hydrogen atom, halogen atom, lower alkoxy, or together represent a methylene dioxy group, $R^2$ and $R^3$ together represent a chemical bond or independently stand for a hydrogen atom, $R^4$ and $R^5$ together with the adjacent nitrogen atom form a 4 to 7 membered ring optionally comprising an oxygen, sulfur or a further nitrogen atom, which ring is optionally substituted by a phenyl, benzyl or $C_{1-3}$ alkyl group and the said substituents may carry a hydroxyl group, one or two methoxy groups, halogen atoms or trifluoromethyl groups, or $R^4$ and $R^5$ together with the adjacent nitrogen atom form a piperidine ring which is optionally substituted by a phenyl or benzyl group and, if desired, it comprises a double bond, $R^6$ stands for hydrogen atom or benzoyl group, and n represents an integer from 3 to 6, acid-addition salts and quaternary ammonium derivatives thereof.

2. Pharmaceutical formulation, which comprises a pharmaceutically effective amount of at least one of compound of formula I as claimed in claim 1, the acid-addition salt and/or quaternary ammonium salt thereof together with one or more pharmaceutically acceptable carriers, diluents and/or excipients.

3. A derivative according to claim 1, wherein said derivative is R,S-2-(E)-phenylmethylene-1-[3-(4-phenylmethyl)-1-piperidinyl-2-hydroxy-propoxyimino]-cyclohexane, an acid addition salt and quaternary ammonium salt thereof.

4. A derivative according to claim 1, wherein said derivative is R,S-2-(E)-phenylmethylene-1-(E)-[3-4-(4-methyl-1-piperazinyl)-2-hydroxy-propoxyimino]- cyclohexane, an acid addition salt and quaternary ammonium salt thereof.

5. A derivative according to claim 1, wherein said derivative is R,S-2-(E)-phenylmethylene-1-(E)-[4-(4-chlorophenyl)-1-piperazinyl]-2-hydroxy-propoxyimino]-cyclohexane, an acid addition salt and quaternary ammonium salt thereof.

6. A derivative according to claim 1, wherein said derivative is R,S-(E)-(2-methoxyphenyl-methylene)-1-(E)-(3-morpholinyl-2-hydroxy-propoxyimino)-cyclohexane and acid addition salts and quaternary ammonium salts thereof.

7. A method of antiarrhythmic, antianginal, stomach secretion inhibiting, local anaesthetic, tranquillo-sedative, antiinflammatory, analgesic and/or calcium antagonisitic treatment, comprising administering to a patient in need of said treatment a therapeutically active amount of a compound of Formula I as defined in claim 1, or an acid addition salt or a quaternary ammonium salt thereof.

* * * * *